(12) United States Patent
Shiroff et al.

(10) Patent No.: US 10,195,419 B2
(45) Date of Patent: Feb. 5, 2019

(54) ELECTRODE LEADS FOR USE WITH IMPLANTABLE NEUROMUSCULAR ELECTRICAL STIMULATOR

(71) Applicant: MAINSTAY MEDICAL LIMITED, Swords, County Dublin (IE)

(72) Inventors: Jason Alan Shiroff, Edina, MN (US); Jason John Skubitz, Arden Hills, MN (US); Prashant Brijmohansingh Rawat, Blaine, MN (US)

(73) Assignee: Mainstay Medical Limited, Swords, County Dublin (IE)

( * ) Notice: Subject to any disclaimer, the term of this patent is extended or adjusted under 35 U.S.C. 154(b) by 0 days.

(21) Appl. No.: 14/453,423

(22) Filed: Aug. 6, 2014

(65) Prior Publication Data

US 2014/0350653 A1    Nov. 27, 2014

Related U.S. Application Data

(63) Continuation-in-part of application No. 14/061,614, filed on Oct. 23, 2013, now Pat. No. 9,072,897, and
(Continued)

(51) Int. Cl.
*A61N 1/05* (2006.01)

(52) U.S. Cl.
CPC ............. *A61N 1/05* (2013.01); *A61N 1/0551* (2013.01); *A61N 1/0558* (2013.01)

(58) Field of Classification Search
CPC .... A61N 1/0551; A61N 1/0558; A61N 1/056; A61N 1/0565; A61N 1/057; A61N 1/0573; A61N 2001/058; A61N 2001/0582
(Continued)

(56) References Cited

U.S. PATENT DOCUMENTS 3,077,884 A    2/1963    Bartow et al.
3,416,534 A    12/1968    Quinn
(Continued)

FOREIGN PATENT DOCUMENTS

CN          1211930 C       7/2005
CN        101678203 A       3/2010
(Continued)

OTHER PUBLICATIONS

Extended European Search Report dated Mar. 5, 2015 in EP Patent Appl Serial No. 14189412.1.
(Continued)

*Primary Examiner* — Allen Porter, Jr.
(74) *Attorney, Agent, or Firm* — Foley & Lardner LLP; Christopher C. Bolten; Nicola A. Pisano

(57) ABSTRACT

An apparatus for neuromuscular electrical stimulation is provided. The apparatus may be a stimulation lead having an elongated member made up of at least one conductor and an insulative sheath surrounding at least a portion of the conductor. A distal portion of the elongated member may include one or more electrodes and at least one fixation element to secure the one or more electrodes in or adjacent to a desired anatomical site for providing stimulation thereto. The stimulation lead has a strain relief portion on the proximal side of the one or more electrodes, configured to reduce axial forces on the distal region of the elongated member, and the effects thereof, to reduce the risk of, or even prevent, displacement of the one or more electrodes and to accommodate localized flexural motion. The apparatus also may include at least one fixation element sized and configured to be deployed between muscle layers to maintain the electrode position at the stimulation site.

23 Claims, 5 Drawing Sheets

Related U.S. Application Data a continuation-in-part of application No. 13/797,100, filed on Mar. 12, 2013.

(60) Provisional application No. 61/659,334, filed on Jun. 13, 2012.

(58) Field of Classification Search
USPC ......... 607/116, 117, 119, 122, 126, 128, 132
See application file for complete search history.

(56) References Cited

U.S. PATENT DOCUMENTS

| | | |
|---|---|---|
| 3,710,777 A | 1/1973 | Sparks |
| 3,754,555 A | 8/1973 | Schmitt |
| 3,875,947 A | 4/1975 | Jula et al. |
| 3,893,463 A | 7/1975 | Williams |
| 3,902,501 A | 9/1975 | Citron et al. |
| 3,976,082 A | 8/1976 | Schmitt |
| 3,999,551 A | 12/1976 | Spitz et al. |
| 4,010,757 A | 3/1977 | Jula et al. |
| 4,026,301 A | 5/1977 | Friedman et al. |
| 4,031,899 A | 6/1977 | Renirie |
| 4,149,528 A | 4/1979 | Murphy |
| 4,235,246 A | 11/1980 | Weiss |
| 4,269,198 A | 5/1981 | Stokes |
| 4,342,317 A | 8/1982 | Axelgaard |
| 4,408,609 A | 10/1983 | Axelgaard |
| 4,418,693 A | 12/1983 | Leveen et al. |
| 4,528,984 A | 7/1985 | Morawetz et al. |
| 4,549,556 A | 10/1985 | Tarjan et al. |
| 4,574,806 A | 3/1986 | McCarthy |
| 4,658,835 A | 4/1987 | Pohndorf |
| 4,832,687 A | 5/1989 | Smith, III |
| 4,917,093 A | 4/1990 | Dufresne et al. |
| 5,069,680 A | 12/1991 | Grandjean |
| 5,199,430 A | 4/1993 | Fang et al. |
| 5,215,088 A | 6/1993 | Normann et al. |
| 5,273,053 A * | 12/1993 | Pohndorf .............. A61N 1/057 604/175 |
| 5,300,108 A * | 4/1994 | Rebell ................ A61N 1/0573 607/127 |
| 5,330,515 A | 7/1994 | Rutecki et al. |
| 5,376,108 A * | 12/1994 | Collins ................ A61N 1/056 604/174 |
| 5,496,345 A | 3/1996 | Kieturakis et al. |
| 5,501,452 A | 3/1996 | Halvorson |
| 5,507,788 A | 4/1996 | Lieber |
| 5,522,854 A | 6/1996 | Ideker et al. |
| 5,569,183 A | 10/1996 | Kieturakis |
| 5,638,825 A | 6/1997 | Yamazaki et al. |
| 5,733,307 A | 3/1998 | Dinsdale |
| 5,741,321 A | 4/1998 | Brennen |
| 5,782,841 A | 7/1998 | Ritz et al. |
| 5,807,234 A | 9/1998 | Bui et al. |
| 5,873,900 A | 2/1999 | Maurer et al. |
| 5,916,172 A | 6/1999 | Hodges et al. |
| 5,957,968 A | 9/1999 | Belden et al. |
| 6,104,957 A | 8/2000 | Alo et al. |
| 6,119,516 A | 9/2000 | Hock |
| 6,314,325 B1 | 11/2001 | Fitz |
| 6,319,241 B1 | 11/2001 | King et al. |
| 6,324,414 B1 | 11/2001 | Gibbons et al. |
| 6,366,819 B1 | 4/2002 | Stokes |
| 6,381,496 B1 | 4/2002 | Meadows et al. |
| 6,406,421 B1 | 6/2002 | Grandjean et al. |
| 6,473,654 B1 | 10/2002 | Chinn |
| 6,516,227 B1 | 2/2003 | Meadows et al. |
| 6,527,787 B1 | 3/2003 | Fogarty et al. |
| 6,565,594 B1 | 5/2003 | Herweck et al. |
| 6,600,954 B2 | 7/2003 | Cohen et al. |
| 6,600,956 B2 | 7/2003 | Maschino et al. |
| 6,605,094 B1 | 8/2003 | Mann et al. |
| 6,671,557 B1 | 12/2003 | Gliner |
| 6,735,474 B1 | 5/2004 | Loeb et al. |
| 6,839,594 B2 | 1/2005 | Cohen et al. |
| 6,845,271 B2 | 1/2005 | Fang et al. |
| 6,862,479 B1 | 3/2005 | Whitehurst et al. |
| 7,018,384 B2 | 3/2006 | Skakoon |
| 7,096,070 B1 | 8/2006 | Jenkins et al. |
| 7,206,641 B2 | 4/2007 | Ignagni et al. |
| 7,218,970 B2 | 5/2007 | Ley et al. |
| 7,239,918 B2 | 7/2007 | Strother et al. |
| 7,286,879 B2 | 10/2007 | Wallace |
| 7,317,948 B1 | 1/2008 | King et al. |
| 7,324,852 B2 | 1/2008 | Barolat et al. |
| 7,324,853 B2 | 1/2008 | Ayal et al. |
| 7,337,005 B2 | 2/2008 | Kim et al. |
| 7,337,006 B2 | 2/2008 | Kim et al. |
| 7,369,894 B2 | 5/2008 | Gerber |
| 7,389,149 B2 * | 6/2008 | Rossing ............... H01R 4/4863 600/377 |
| 7,444,181 B2 | 10/2008 | Shi et al. |
| 7,447,546 B2 | 11/2008 | Kim et al. |
| 7,450,993 B2 | 11/2008 | Kim et al. |
| 7,489,561 B2 | 2/2009 | Armstrong et al. |
| 7,493,175 B2 | 2/2009 | Cates et al. |
| 7,499,746 B2 | 3/2009 | Buhlmann et al. |
| 7,502,651 B2 | 3/2009 | Kim et al. |
| 7,580,753 B2 | 8/2009 | Kim et al. |
| 7,668,598 B2 | 2/2010 | Herregraven et al. |
| 7,684,866 B2 | 3/2010 | Fowler et al. |
| 7,708,763 B2 | 5/2010 | Selover et al. |
| 7,761,166 B2 | 7/2010 | Giftakis et al. |
| 7,792,591 B2 | 9/2010 | Rooney et al. |
| 7,797,053 B2 | 9/2010 | Atkinson et al. |
| 7,813,803 B2 | 10/2010 | Heruth et al. |
| 7,908,015 B2 | 3/2011 | Lazeroms et al. |
| 7,917,230 B2 | 3/2011 | Bly |
| 7,930,039 B2 | 4/2011 | Olson |
| 7,981,144 B2 | 7/2011 | Geist et al. |
| 8,016,846 B2 | 9/2011 | McFarlin et al. |
| 8,065,020 B2 | 11/2011 | Ley et al. |
| 8,082,039 B2 | 12/2011 | Kim et al. |
| 8,170,690 B2 | 5/2012 | Morgan et al. |
| 8,229,565 B2 | 7/2012 | Kim et al. |
| 8,229,656 B2 | 7/2012 | Ikushima et al. |
| 8,249,701 B2 | 8/2012 | Imran et al. |
| 8,249,713 B2 | 8/2012 | Fang et al. |
| 8,380,318 B2 | 2/2013 | Kishawi et al. |
| 8,391,966 B2 | 3/2013 | Luo et al. |
| 8,409,233 B1 | 4/2013 | Chinn et al. |
| 8,428,728 B2 | 4/2013 | Sachs |
| 8,463,383 B2 | 6/2013 | Sakai et al. |
| 8,498,697 B2 | 7/2013 | Yong et al. |
| 8,606,358 B2 | 12/2013 | Sachs |
| 8,798,005 B1 | 8/2014 | Vargantwar et al. |
| 8,886,337 B2 | 11/2014 | Bennett et al. |
| 8,965,516 B2 | 2/2015 | Bennett et al. |
| 9,072,897 B2 | 7/2015 | Sachs et al. |
| 9,079,019 B2 | 7/2015 | Crosby et al. |
| 9,108,053 B2 | 8/2015 | Crosby et al. |
| 9,320,847 B2 | 4/2016 | Rooney et al. |
| 9,561,364 B2 * | 2/2017 | Bondhus ............... A61N 1/08 |
| 9,861,811 B2 | 1/2018 | Crosby et al. |
| 2001/0053885 A1 | 12/2001 | Gielen et al. |
| 2002/0065543 A1 * | 5/2002 | Gomperz ............... A61N 1/057 607/115 |
| 2002/0099419 A1 | 7/2002 | Cohen et al. |
| 2002/0115945 A1 | 8/2002 | Herman et al. |
| 2002/0147485 A1 | 10/2002 | Mamo et al. |
| 2002/0156513 A1 | 10/2002 | Borkan |
| 2002/0161415 A1 | 10/2002 | Cohen et al. |
| 2002/0183765 A1 | 12/2002 | Adams |
| 2003/0100933 A1 | 5/2003 | Ayal et al. |
| 2003/0120328 A1 | 6/2003 | Jenkins et al. |
| 2003/0199938 A1 | 10/2003 | Smits et al. |
| 2004/0030360 A1 | 2/2004 | Eini et al. |
| 2004/0097986 A1 | 5/2004 | Adams |
| 2004/0111118 A1 | 6/2004 | Hill et al. |
| 2004/0122482 A1 | 6/2004 | Tung et al. |
| 2004/0147969 A1 | 7/2004 | Mann et al. |
| 2004/0167580 A1 | 8/2004 | Mann et al. |
| 2004/0214790 A1 | 10/2004 | Borgens |

(56) References Cited

U.S. PATENT DOCUMENTS

| | | |
|---|---|---|
| 2004/0230281 A1* | 11/2004 | Heil ............... A61B 17/320068 607/126 |
| 2004/0236383 A1 | 11/2004 | Yelizarov |
| 2005/0070971 A1 | 3/2005 | Fowler et al. |
| 2005/0075701 A1 | 4/2005 | Shafer |
| 2005/0080472 A1 | 4/2005 | Atkinson et al. |
| 2005/0107861 A1 | 5/2005 | Harris et al. |
| 2005/0119713 A1 | 6/2005 | Whitehurst et al. |
| 2005/0149154 A1 | 7/2005 | Cohen et al. |
| 2005/0154389 A1 | 7/2005 | Selover et al. |
| 2005/0165456 A1 | 7/2005 | Mann et al. |
| 2005/0177211 A1 | 8/2005 | Leung et al. |
| 2005/0240243 A1 | 10/2005 | Barolat et al. |
| 2005/0246006 A1 | 11/2005 | Daniels |
| 2005/0283204 A1 | 12/2005 | Buhlmann et al. |
| 2006/0004429 A1 | 1/2006 | Mrva et al. |
| 2006/0009810 A1 | 1/2006 | Mann et al. |
| 2006/0009827 A1 | 1/2006 | Kurth et al. |
| 2006/0032657 A1* | 2/2006 | Zarembo ............... A61N 1/056 174/69 |
| 2006/0052856 A1 | 3/2006 | Kim et al. |
| 2006/0106416 A1 | 5/2006 | Raymond et al. |
| 2006/0111746 A1 | 5/2006 | Foreman et al. |
| 2006/0111754 A1 | 5/2006 | Rezai et al. |
| 2006/0155341 A1 | 7/2006 | Tehrani et al. |
| 2006/0184222 A1 | 8/2006 | Camps et al. |
| 2006/0206166 A1 | 9/2006 | Weiner |
| 2006/0235484 A1 | 10/2006 | Jaax et al. |
| 2006/0241716 A1 | 10/2006 | Finch et al. |
| 2006/0259074 A1 | 11/2006 | Kelleher et al. |
| 2007/0027501 A1 | 2/2007 | Jensen et al. |
| 2007/0049980 A1* | 3/2007 | Zielinski ............... A61B 5/0215 607/23 |
| 2007/0060967 A1 | 3/2007 | Strother et al. |
| 2007/0073357 A1 | 3/2007 | Rooney et al. |
| 2007/0100377 A1 | 5/2007 | Armstrong et al. |
| 2007/0100391 A1 | 5/2007 | Armstrong |
| 2007/0100408 A1 | 5/2007 | Gerber |
| 2007/0100411 A1 | 5/2007 | Bonde |
| 2007/0123954 A1 | 5/2007 | Gielen et al. |
| 2007/0129780 A1 | 6/2007 | Whitehurst et al. |
| 2007/0135768 A1 | 6/2007 | Carlsen |
| 2007/0179557 A1 | 8/2007 | Maschino et al. |
| 2007/0208392 A1 | 9/2007 | Kuschner et al. |
| 2007/0232936 A1 | 10/2007 | Mann et al. |
| 2007/0239224 A1 | 10/2007 | Bennett et al. |
| 2008/0026981 A1 | 1/2008 | Muhrer et al. |
| 2008/0103573 A1 | 5/2008 | Gerber |
| 2008/0103579 A1 | 5/2008 | Gerber |
| 2008/0132961 A1 | 6/2008 | Jaax et al. |
| 2008/0132969 A1 | 6/2008 | Bennett et al. |
| 2008/0167698 A1 | 7/2008 | Kim et al. |
| 2008/0177351 A1 | 7/2008 | Fang et al. |
| 2008/0183221 A1 | 7/2008 | Burdulis |
| 2008/0183257 A1 | 7/2008 | Imran et al. |
| 2008/0200972 A1 | 8/2008 | Rittman et al. |
| 2008/0228241 A1 | 9/2008 | Sachs |
| 2008/0234791 A1 | 9/2008 | Arle et al. |
| 2008/0269716 A1 | 10/2008 | Bonde et al. |
| 2008/0269812 A1 | 10/2008 | Gerber et al. |
| 2009/0005833 A1 | 1/2009 | Cameron et al. |
| 2009/0018576 A1 | 1/2009 | Binmoeller |
| 2009/0020764 A1 | 1/2009 | Anderson et al. |
| 2009/0112263 A1 | 4/2009 | Pool et al. |
| 2009/0192567 A1 | 7/2009 | Armstrong et al. |
| 2009/0210041 A1 | 8/2009 | Kim et al. |
| 2009/0248095 A1* | 10/2009 | Schleicher ............ A61N 1/0558 607/2 |
| 2009/0254095 A1 | 10/2009 | Levine et al. |
| 2009/0259280 A1 | 10/2009 | Wilkin et al. |
| 2009/0299201 A1 | 12/2009 | Gunderson |
| 2009/0326613 A1 | 12/2009 | Knoblich |
| 2010/0030227 A1 | 2/2010 | Kast et al. |
| 2010/0036280 A1 | 2/2010 | Ballegaard et al. |
| 2010/0036454 A1 | 2/2010 | Bennett et al. |
| 2010/0082086 A1 | 4/2010 | Zhu |
| 2010/0114206 A1 | 5/2010 | Kaemmerer et al. |
| 2010/0137938 A1 | 6/2010 | Kishawi et al. |
| 2010/0152808 A1 | 6/2010 | Boggs, II |
| 2010/0152809 A1 | 6/2010 | Boggs, II |
| 2010/0174240 A1 | 7/2010 | Wells et al. |
| 2010/0174326 A1 | 7/2010 | Selover et al. |
| 2010/0179562 A1 | 7/2010 | Linker et al. |
| 2010/0185161 A1 | 7/2010 | Pellegrino et al. |
| 2010/0211149 A1 | 8/2010 | Morgan et al. |
| 2010/0249875 A1 | 9/2010 | Kishawi et al. |
| 2010/0280576 A1 | 11/2010 | Gerber et al. |
| 2010/0292769 A1 | 11/2010 | Brounstein et al. |
| 2011/0004269 A1 | 1/2011 | Strother et al. |
| 2011/0021943 A1 | 1/2011 | Lacour et al. |
| 2011/0022114 A1 | 1/2011 | Navarro |
| 2011/0022123 A1 | 1/2011 | Stancer et al. |
| 2011/0054565 A1 | 3/2011 | Wacnik et al. |
| 2011/0106207 A1 | 5/2011 | Cauller et al. |
| 2011/0160538 A1 | 6/2011 | Ravikumar et al. |
| 2011/0190786 A1 | 8/2011 | Gerber et al. |
| 2011/0224665 A1 | 9/2011 | Crosby et al. |
| 2011/0224682 A1 | 9/2011 | Westlund et al. |
| 2011/0251662 A1 | 10/2011 | Griswold et al. |
| 2011/0257660 A1 | 10/2011 | Jones et al. |
| 2011/0270340 A1 | 11/2011 | Pellegrini et al. |
| 2012/0035953 A1 | 2/2012 | Armstrong |
| 2012/0089153 A1 | 4/2012 | Christopherson et al. |
| 2012/0116477 A1 | 5/2012 | Crowe et al. |
| 2012/0192874 A1 | 8/2012 | Bolea et al. |
| 2012/0215218 A1 | 8/2012 | Lipani |
| 2012/0283800 A1 | 11/2012 | Perryman et al. |
| 2012/0290055 A1 | 11/2012 | Boggs, II |
| 2012/0310140 A1 | 12/2012 | Kramer et al. |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2012/0323253 A1 | 12/2012 | Garai et al. |
| 2013/0023974 A1 | 1/2013 | Amrani |
| 2013/0053926 A1 | 2/2013 | Hincapie Ordonez et al. |
| 2013/0096641 A1 | 4/2013 | Strother et al. |
| 2013/0131766 A1 | 5/2013 | Crosby et al. |
| 2013/0155117 A1 | 6/2013 | Bang |
| 2013/0197607 A1 | 8/2013 | Wilder et al. |
| 2013/0197615 A1 | 8/2013 | Rundle et al. |
| 2013/0211487 A1 | 8/2013 | Fang et al. |
| 2013/0218247 A1 | 8/2013 | Sachs |
| 2013/0238066 A1 | 9/2013 | Boggs et al. |
| 2013/0245715 A1 | 9/2013 | Peterson |
| 2013/0261696 A1 | 10/2013 | Thacker et al. |
| 2013/0296966 A1 | 11/2013 | Wongsarnpigoon et al. |
| 2013/0310901 A1 | 11/2013 | Perryman et al. |
| 2013/0338730 A1 | 12/2013 | Shiroff et al. |
| 2014/0039574 A1 | 2/2014 | Bradley |
| 2014/0046398 A1 | 2/2014 | Sachs et al. |
| 2014/0058476 A1 | 2/2014 | Crosby et al. |
| 2014/0114385 A1 | 4/2014 | Nijhuis et al. |
| 2014/0288616 A1 | 9/2014 | Rawat et al. |
| 2015/0105840 A1 | 4/2015 | Boggs, II |
| 2015/0306405 A1 | 10/2015 | Sachs et al. |
| 2015/0374992 A1 | 12/2015 | Crosby et al. |
| 2016/0045746 A1 | 2/2016 | Jiang et al. |
| 2016/0045747 A1 | 2/2016 | Jiang et al. |
| 2016/0067476 A1 | 3/2016 | Rawat et al. |
| 2016/0106994 A1 | 4/2016 | Crosby et al. |
| 2016/0213927 A1 | 7/2016 | McGee et al. |

FOREIGN PATENT DOCUMENTS

| | | |
|---|---|---|
| EP | 0 587 269 B1 | 12/1998 |
| EP | 1 053 762 B1 | 11/2000 |
| EP | 1 255 583 B1 | 11/2002 |
| EP | 2 125 100 A1 | 12/2009 |
| EP | 2 273 931 A1 | 1/2011 |
| WO | WO-01/58520 A1 | 8/2001 |
| WO | WO-2004/066820 A2 | 8/2004 |
| WO | WO-2006/091611 A1 | 8/2006 |
| WO | WO-2006/133445 A2 | 12/2006 |
| WO | WO-2006/135791 A2 | 12/2006 |

(56) References Cited

FOREIGN PATENT DOCUMENTS

| | | |
|---|---|---|
| WO | WO-2007/051146 A1 | 5/2007 |
| WO | WO-2007/138598 A2 | 12/2007 |
| WO | WO-2008/048471 A2 | 4/2008 |
| WO | WO-2008/070807 A2 | 6/2008 |
| WO | WO-2008/094952 A2 | 8/2008 |
| WO | WO-2008/112178 A1 | 9/2008 |
| WO | WO-2009/020764 A1 | 2/2009 |
| WO | WO-2009/134475 A1 | 11/2009 |
| WO | WO-2010/062600 A2 | 6/2010 |
| WO | WO-2010/062622 A2 | 6/2010 |
| WO | WO-2011/079866 A1 | 7/2011 |
| WO | WO-2011/112773 A2 | 9/2011 |
| WO | WO-2012/057916 A1 | 5/2012 |
| WO | WO-2012/091747 A1 | 7/2012 |
| WO | WO-2013/016268 A1 | 1/2013 |
| WO | WO-2013/019853 A1 | 2/2013 |
| WO | WO-2013/036630 A1 | 3/2013 |
| WO | WO-2013/096260 A1 | 6/2013 |
| WO | WO-2013/155117 A1 | 10/2013 |
| WO | WO-2014/099423 A1 | 6/2014 |
| WO | WO-2015/059570 A1 | 4/2015 |
| WO | WO-2015/187426 A1 | 12/2015 |
| WO | WO-2018/007914 A1 | 1/2018 |

OTHER PUBLICATIONS

Gazelle et al., "Tumor Ablation with radio-frequency Energy," Radiology, (2000), 217(3):633-646.
Gondin, et al., Electromyostimulation training effects on neural drive and muscle architecture, Med. Sci. Sports. Exerc., 37(8):1291-9 (2005).
Haemmerich et al., "Thermal Tumor Ablation: Devices, Clinical Applications and Future Directions," Int. J. Hyperthermia, (2005) 21(8):775-760 (Abstract).
Informal Response to Written Opinion dated Jan. 17, 2012 in Int'l PCT Patent Appl. Serial No. PCT/US2011/027834.
International Search Report & Written Opinion dated Jan. 19, 2016 in Int'l PCT Patent Appl. Serial No. PCT/IB2015/055926.
International Search Report & Written Opinion dated Mar. 19, 2015 in Int'l PCT Patent Appln Serial No. PCT/IB2014/002920.
International Search Report & Written Opinion dated Apr. 5, 2013 in Int'l PCT Patent Application Serial No. PCT/US2012/070259.
International Search Report and Written Opinion dated Jan. 26, 2016 in Int'l PCT Patent Appl. Serial No. PCT/IB2015/057838.
International Search Report and Written Opinion dated Oct. 16, 2015 in Int'l PCT Patent Appl Serial No. PCT/US2015/032732.
International Search Report dated Oct. 19, 2011 in Int'l PCT Patent Appl. Serial No. PCT/US2011/027934.
Int'l Preliminary Report on Patentability dated May 28, 2014 in Int'l PCT Patent Appl No. PCT/US2012/070259.
Lieber, Richard, Comparison between animal and human studies of skeletal muscle adaptation to chronic stimulation, Clinical Orthopaedics and related research, No. 233, pp. 19-24 (1988).
Lieber, Richard, Skeletal muscle adaptability. II: Muscle properties following spinal-cord injury, Developmental medicine and Child Neurology 28(4):533-42 (1986).
Lieber, Richard, Skeletal muscle adaptability. III: Muscle properties following chronic electrical stimulation, Developmental medicine and Child Neurology 28(5):662-70 (1986).
Partial International Search Report dated Aug. 4, 2015 in Int'l PCT Patent Appl Serial No. PCT/US2015/032732.
Rosatelli, et al., Three-dimensional study of the musculotendinous architecture of lumbar multifidus and its functional implications, Clinical Anatomy 21(6):539-44 (2008).
Sippl, Charles J., "Computer Dictionary: Third Edition," pp. 2257 and 340.
Sluijter, "Radiofrequency Ablation in the Management of Spinal Pain," C212, (2006), IV(1):10-15.
Wikipedia, "Interference Fit," http://en.wikipedia.org/wiki/Interference_fit, accessed Dec. 4, 2014.
Wikipedia, "Time-division multiplexing," https://en.wikipedia.org/wiki/Time-division_multiplexing (accessed Nov. 12, 2015).
Written Opinion dated Feb. 3, 2014 in Int'l PCT Patent Appl. Serial No. PCT/US2012/070259.
Written Opinion dated Nov. 16, 2011 in Int'l PCT Patent Appl. Serial No. PCT/US2011/027934.
Airaksinen et al., "Chapter 4. European guidelines for the management of chronic nonspecific low back pain," European spine journal [I: official publication of the European Spine Society, the European Spinal Deformity Society, and the European Section of the Cervical Spine Research Society 15 Suppl 2 (2006):S192-300. http://www.ncbi.nlm.nih.gov/pubmed/16550448.
Baker et al., "Clinical Uses of Neuromuscular Electrical Stimulation," NeuroMuscular Electrical Stimulation—A Practical Guide, 4th ed. Rancho Los Amimgos Research and Education Institute Inc., pp. 47-66 (2000).
Bhadra et al., "Peripheral nerve stimulation for restoration of motor function," Journal of Clinical Neurophysiology: Official Publication of the American Electroencephalographic Society, 14(5):378-33 (Sep. 1997).
Bogie et al., "Effects of regular use of neuromuscular electrical stimulation on tissue health," Journal of Rehabilitation Research and Development, 40(6):469-475 (2003) available at: http://www.ncbi.nlm.nih.gov/pubmed/15077659 (Accessed Jan. 18, 2011).
Bowman et al., "Effects of Waveform Parameters on Comfort during Transcutaneous Neuromuscular Electrical Stimulation," Annals of Biomedical Engineering, 13:59-74 (1985).
Bradford et al., "Surface Electrical Stimulation in the Treatment of Idiopathic Scoliosis: Preliminary Results in 30 Patients," Spine, 8(7):757-764 (1983).
Brazier et al., "A Comparison of the EQ-5D and SF-6D Across Seven Patient Groups," Health Economics, 13:873-884 (2004).
Coghlan et al., "Electrical muscle stimulation for deep stabilizing muscles in abdominal wall," Conference proceedings: . . . Annual International Conference of the IEEE Engineering in Medicine and Biology Society. IEEE Engineering in Medicine and Biology Society. Conference, pp. 2756-2759 (2008) available at: http://www.ncbi.nlm.nih.gov/pubmed/19163276.
Coghlan et al., "Neuromuscular electrical stimulation training results in enhanced activation of spinal stabilizing muscles during spinal loading and improvements in pain ratings," Conference proceedings: . . . Annual International Conference of the IEEE Engineering in Medicine and Biology Society. IEEE Engineering in Medicine and Biology Society. Conference, pp. 7622-7625 (2011) available at: http://www.ncbi.n1m.nih.gov/pubmed/22256103.
Crago et al., "The choice of pulse duration for chronic electrical stimulation via surface, nerve, and intramuscular electrodes," Annals of Biomedical Engineering, 2(3):252-264 (1974).
Criterion Inc., "NMES Treatment Protocols," 3 pages (accessed Jun. 7, 2012) available at http://www.criterionmed.com/PDF/NMES%20Treatment%20Protocols.pdf.
Durham et al., "Surface Electrical Stimulation Versus Brace in Treatment of Idiopathic Scoliosis," Spine, 15(9):888-891 (1990).
Empi, "Low Back Syndrome/Chronic Low Back Pain," NMES Guidelines for Treatment, 2 pages (2003).
Ferreira et al., "Comparison of general exercise, motor control exercise and spinal manipulative therapy for chronic low back pain: A randomized trial," Pain, 131(1-2):31-37 (2007) available at: http://www.ncbi.nlm.nih.gov/pubmed/17250965.
Freeman, et al., The Role of the Lumbar Multifidus in Chronic Low Back Pain: A Review, American Academy of Physical Medicine and Rehabilitation, 2:142-146 (2010).
Friedman et al., "Electrical stimulation for scoliosis," American Family Physician, 25(4):155-160 (1982) available at: http://www.ncbi.n1m.nih.gov/pubmed/6978055 (Accessed Oct. 19, 2011).
Garmirian, et al., Discriminating Neurogenic from Myopathic Disease via Measurement of Muscle Anisotrophy, Muscle Nerve, 39(1):16-24 (2009) (Abstract only).
Glaser et al., "Electrical Muscle Stimulation as an Adjunct to Exercise Therapy in the Treatment of Nonacute Low Back Pain: A Randomized Trial," The Journal of Pain, 2(5):295-300 (2001).

(56) References Cited

OTHER PUBLICATIONS

Gorman et al., "The effect of stimulus parameters on the recruitment characteristics of direct nerve stimulation," IEEE Transactions on Bio-medical Engineering, 30(7):407-414 (1983).
Hagg et al., "The Clinical Importance of Changes in Outcome Scores After Treatment for Chronic Low Back Pain," Eur. Spine. J., 12:12-20 (2003).
Herbert et al., "Scoliosis Treatment in Children Using a Programmable, Totally Implantable Muscle Stimulator (ESI)," IEEE Transactions on Biomedical Engineering, 36(7):801 (Jul. 1989).
Hodges et al., "Response of the deep paraspinal muscles to cortical but not transmastoid stimulation is increased at a single lumbar level following interverebral disc lesion," Progress in Motor Control Vi—Brazil. 36:2-3 (2007).
Hodges, et al., Intervetebral Stiffness of the Spine is Increased by Evoked Contraction of Transversus Abdominis and the Diaphragm: In Vivo Porcine Studies, Spine 28(23):2594-2601 (2003) (Abstract only).
Hodges, Is There a Role for Transversus Abdominis in Lumbo-Pelvis Stability? Manual Therapy, 4(2):74-86 (1999).
Holm, et al., Sensorimotor Control of the Spine, J. Electromyogr. Kinesiol. 12(3):219-34 (2002) (Abstract only).
Hortobagyi et al., "Neural adaptations to electrical stimulation strength training," European Journal of Applied Physiology, 2439-2449 (2011) available at: http://www.ncbi.nlm.nih.gov/pubmed/21643920 (Accessed Jul. 19, 2011).
Keller, et al., Muscular Contributions to Dynamic Dorsoventral Lumber Spine Stiffness, Eur. Spine J., 16(2):245-54 (2007).
Kiesel et al., "Measurement of lumbar multifidus muscle contraction with rehabilitative ultrasound imaging," Manual Therapy, 12(2):161-166 (2007) available at: http://www.ncbi.nlm.nih.gov/pubmed/16973400.
Lauridsen et al., "Responsiveness and Minimal Clinically Important Difference for Pain and Disability Instruments in Low Back Pain Patients," BMC Musculoskeletal Disorders, 7(82):16 pages (2006).
Miyatani, et al., Validity of Estimating Limb Muscle Volume By Bioelectrical Impedance, J. Appl. Physiol., 91:386-394 (2001).
Mortimer et al., "Intramuscular electrical stimulation: tissue damage," Annals of Biomedical Engineering, 8(3):235-244 (1980).
Mortimer et al., "Peripheral Nerve and Muscle Stimulation. In: Horch KW, Dhillon G, eds," Neuroprosthetics: Theory and Practice (Series on Bioengineering & Biomedical Engineering—vol. (2), World Scientific Publishing Company, pp. 1-48 (2005).
Nachemson et al., "Effectiveness of Treatment with a Brace in Girls Who Have Adolescent Idiopathic Scoliosis," The Journal of Bone and Joint Surgery, 77-A(6):815-819 (Jun. 1995).
Oaao Bock, "ActiGait Implantable Drop Foot Stimulator," Surgeon Manual, 28 pages (2006).
O'Donnell et al., "Electrical Stimulation in the Treatment of Idiopathic Scoliosis," Clinical Orthopaedics and Related Research, No. 229:107-112 (Apr. 1988).
Paicius et al., "Peripheral Nerve Field Stimulation for the Treatment of Chronic Low Back Pain: Preliminary Results of Long-Term Follow-up: A Case Series," Neuromodulation, 10(3):279-290 (2007) available at: http://www.blackwell-synergy.com/doi/abs/l0.llll/j.1525-1403.2007.00116.x.
Panjabi, Manohar, "A hypothesis of chronic back pain: ligament subfailure injuries lead to muscle control dysfunction," European spine journal: official publication of the European Spine Society, the European Spinal Deformity Society, and the European Section of the Cervical Spine Research Society 15, No. 5 (May 2006): 668-676. http://www.ncbi.nlm.nih.gov/pubmed/16047209.
Panjabi, Manohar, "The stabilizing system of the spine. Part 1. Function, dysfunction, adaptation, and enhancement," Journal of Spinal Disorders, 5(4)383-389 (Dec. 1992), Discussion 397. http://www.ncbi.nlm.nih.gov/pubmed/1490034.
Panjabi, Manohar, "The stabilizing system of the spine. Part II. Neutral zone and instability hypothesis," Journal of Spinal Disorders, 5(4):390-396 (Dec. 1992), Discussion 397. http://www.ncbi.nlm.nih.gov/pubmed/1490035.

PCT International Search Report and Written Opinion dated Sep. 3, 2013 in related PCT Application No. PCT/US2013/045223.
Peckham et al., "Functional electrical stimulation for neuromuscular applications," Annual review of Biomedical Engineering, 7:327-360 (2005) available at: http://www.ncbi.nlm.nih.gov/pubmed/16004574.
Peterson et al., "Long-term intramuscular electrical activation of the phrenic nerve: safety and reliability," IEEE Transactions on Biomedical Engineering, 41(12):1115-1126 (1994).
Poitras et al., "Evidence-informed management of chronic low back pain with transcutaneous electrical nerve stimulation, interferential current, electrical muscle stimulation, ultrasound, and thermotherapy," The Spine Journal 8:226-233 (2008).
Reed B., :The Physiology of Neuromuscular Electrical Stimulation, Pediatric Physical Therapy, 9(3):96-102 (1997) available at: http://journals.lww.com/pedpt/pages/articleviewer.aspx?year=1997&issue=00930&article=00002&type=abstract.
RS Medical, "RS-4M Muscle Stimulator," available at http://www.rsmedical.com/documents/fact_sheet_RS4m.pdf (last visited Jul. 19, 2012).
Rutkove, "Electrical Impedance Myography: Background, Current State, and Future Directions," Muscle Nerve, 40(6):936-946 (2009).
Schwartz et al., "Therapeutic Electrical Stimulation of the Hypoglossal Nerve in Obstructive Sleep Apnea," Arch Otolaryngal Head Neck Surg., 127:1216-1223 (2001).
Sheffler et al., "Neuromuscular Electrical Stimulation in Neurorehabilitation," Muscle Nerve, 35: 562-590 (2007).
Solomonow et al., "The Ligamento-Muscular Stabilizing System of the Spine," Spine, (1998), 23(23):2552-2562.
Spinal Fusion Guidelines, MD Guidelines, 2009. www.mdguidelines.com/spinal-fusion.
Stokes, et al., "Surface EMG Electrodes Do Not Accurately Record from Lumbar Multifidus Muscles," Clin. Biomech, (2003), 18(1):9-13 (Abstract Only).
Van Dieen, et al., "Trunk Muscle Recruitment Patterns," Spine, (2003), 28(8):834-841 (Abstract Only).
Van et al., "The use of real-time ultrasound imaging for biofeedback of lumbar multifidus muscle contraction in healthy subjects," The Journal of Orthopaedic and Sports Physical Therapy, 36(12):920-925 (2006) available at: http://www.ncbi.nlm.nih.gov/pubmed/17193869.
Van Zundert et al., "Radiofrequency treatment for chronic pain syndromes," CPD Anaesthesis, 6(1):13-17 (2004).
Verrills et al., "Peripheral Nerve Stimulation: A Treatment for Chronic Low Back Pain and Failed Back Surgery Syndrome?," Neuromodulation: Technology at the Neural Interface, (2009), 12(1):68-75.
Vrbova et al., Application of Muscle/Nerve Stimulation in Health and Disease, Springer Verlag (2008) available at: http://books.google.com/books?hl=en&lr=&id=jb8fDGxkbqEC&oi=fnd&pg=PAI&dq=Application of Muscle/Nerve Stimulation in Health and Disease&ots=CMV5rXiDQD&sig=Wg8u1YOC4PgvVDzcjdwBub5U2To (Accessed Jun. 2, 2011).
Wallwork et al., "The effect of chronic low back pain on size and contraction of the lumbar multifidus muscle," Manual Therapy, 14(5):496-500 (2009) available at: http://www.ncbi.nlm.nih.gov/pubmed/19027343.
Ward et al., "Architectural analysis and intraoperative measurements demonstrate the unique design of the multifidus for lumbar spine stability," J. Bone Joint Surg. [Am.] 91:176-185, PMC2663324 (2009).
Wright et al., "Morphologic and histochemical characteristics of skeletal muscle after long-term intramuscular electrical stimulation," Spine, 17(7):767-770 (1992) available at: http://www.ncbi.nlm.nih.gov/pubmed/1502640 (Accessed Aug. 2, 2011).
U.S. Appl. No. 15/202,435, filed Jul. 5, 2016, Beck et al.
U.S. Appl. No. 15/202,485, filed Jul. 5, 2016, Beck et al.
Medtronic Extension Passer 3555 Accessory Kit—Technical Instructions, 2 pages (2001).
Medtronic Interstim Therapy 3093 & 3889—Implant Manual, 38 pages (2010).
Medtronic Model 3464 Receiver/Extension Internalization Manual, SE-4 for Spinal Cord Stimulation (SCS), 7 pages (1986).

(56) References Cited

OTHER PUBLICATIONS

Deckers, et al., Chronic Low Back Pain: Restoration of Dynamic Stability, Neuromodulation, 18:478-486 (2015).
International Search Report & Written Opinion dated Sep. 28, 2017 in Int'l PCT Patent Appl. Serial No. PCT/IB2017/053945.
International Search Report & Written Opinion dated Oct. 20, 2017 in Int'l PCT Patent Appl. Serial No. PCT/IB2017/053946.
MicroProbes for Life Science, Nerve Cuff electrodes,2018, available at https://microprobes.com/products/peripheral-electrodes/nerve-cuff, accessed Mar. 5, 2018.
Unit III—The Spine, "Motions of the Spine," available at https://courses.vcu.edu/DANC291-003/unit_3.htm, accessed Mar. 5, 2018.
U.S. Appl. No. 12/075,174, filed Mar. 10, 2008, now U.S. Patent No. 8,428,728 dated Apr. 23, 2013.
U.S. Appl. No. 13/045,421, filed Mar. 10, 2011, now U.S. Patent No. 9,248,278 dated Feb. 2, 2016.
U.S. Appl. No. 13/045,435, filed Mar. 10, 2011.
U.S. Appl. No. 13/564,584, filed Aug, 1, 2012, now U.S. Patent No. 9,079,019 dated Jul. 14, 2015.
U.S. Appl. No. 13/718,806, filed Dec. 18, 2012, now U.S. Patent No. 9,108,053 dated Aug. 18, 2015.
U.S. Appl. No. 13/797,100, filed Mar. 12, 2013.
U.S. Appl. No. 13/858,809, filed Apr. 8, 2013, now U.S. Patent No. 8,606,358 dated Dec. 10, 2013.
U.S. Appl No. 14/061,614, filed Oct. 23, 2013, now U.S. Patent No. 9,072,897 dated Jul. 7, 2015.
U.S. Appl. No. 14/295,153, filed Jun. 30, 2014, now U.S. Patent No. 9,186,153 dated Nov. 17, 2015.
U.S. Appl. No. 14/792,430, filed Jul. 6, 2015.
U.S. Appl. No. 14/849,478, filed Sep. 9, 2015.
U.S. Appl. No. 14/882,087, filed Oct. 13, 2015.
U.S. Appl. No. 14/939,955, filed Nov. 12, 2015.
U.S. Appl. No. 15/202,435, filed Jul. 5, 2016.
U.S. Appl. No. 15/202,485, filed Jul. 5, 2016.

* cited by examiner

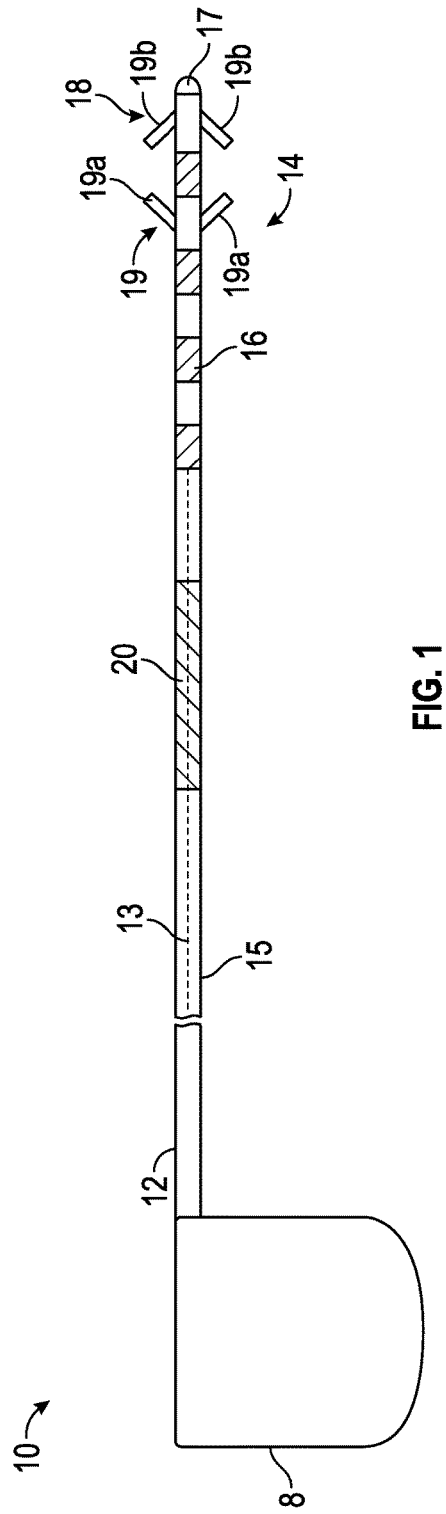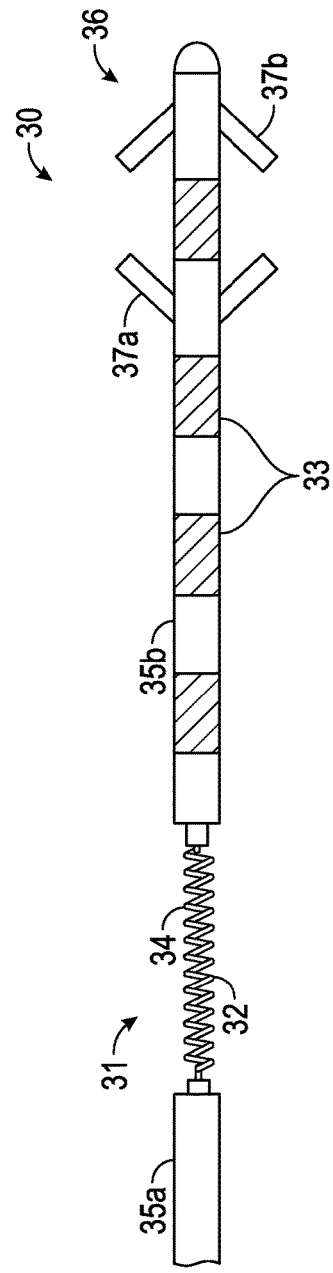
FIG. 1
FIG. 2

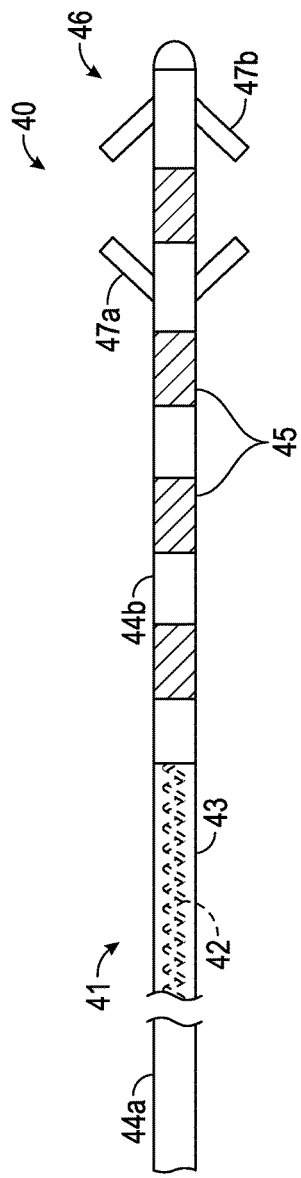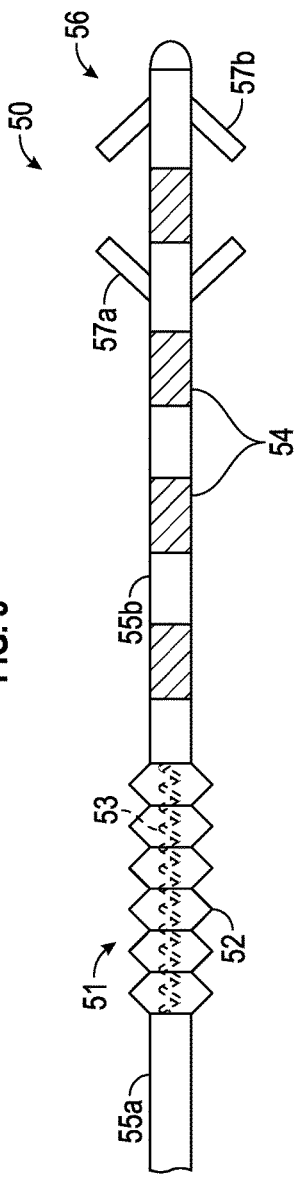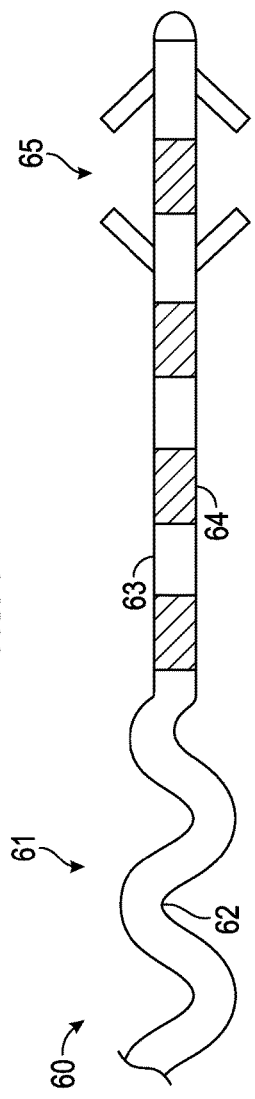

ELECTRODE LEADS FOR USE WITH IMPLANTABLE NEUROMUSCULAR ELECTRICAL STIMULATOR

I. CROSS-REFERENCE TO RELATED APPLICATIONS

This application is a continuation-in-part application of U.S. patent application Ser. No. 14/061,614, filed Oct. 23, 2013, the entire contents of which is incorporated herein by reference. This application is also a continuation-in-part application of U.S. patent application Ser. No. 13/797,100, filed Mar. 12, 2013, which claims the benefit of priority of U.S. Provisional Application Ser. No. 61/659,334, filed Jun. 13, 2012, the entire contents of each of which is incorporated herein by reference.

II. FIELD OF THE INVENTION

This application generally relates to an apparatus for providing a lead for neuromuscular stimulation that is configured to limit axial forces and tensile load on a distal end of the lead and to reduce movement of the stimulation electrodes.

III. BACKGROUND OF THE INVENTION

Many medical devices incorporate an elongated or tubular element that is required to be positioned at a particular anatomical site. Such devices include pacemakers, spinal cord and peripheral nerve stimulators for parathesia systems and functional electrical stimulation, and drug delivery catheters.

In the case of a pacemaker, for example, the leads may be threaded through a vein, and then anchored using a fixation element at the distal tip of the lead to reduce the risk of, or even prevent, dislodgement. Such a fixation element may be a tine, fin, or screw that is secured in the trabeculae or muscle tissue of the ventricle, atrium or cardiac vessel.

Sacral nerve stimulator leads may include a fixation element(s), such as a tine(s), projecting from the lead body to constrain movement of the lead body relative to the surrounding tissue. Tines on a sacral nerve lead, such as the InterStim™ lead available from Medtronic, Inc. of Fridley, Minn., generally are located at a substantial proximal distance from the electrodes and face in only one (proximal) direction. Such placement allows for relative movement of the electrodes as the muscle and connective tissue within which the tines are placed moves relative to the stimulation target.

A spinal cord stimulator (SCS) may include an implantable pulse generator (IPG) connected to one or more leads having one or more electrodes configured to deliver electrical energy to the spinal cord to block pain signals from reaching the brain. Small changes in electrode position may in some cases adversely impact the ability of such systems to effectively deliver therapy. It may not be practical or feasible to provide an anchoring mechanism inside the spinal canal to anchor a lead of the SCS. One conventional technique for securing the lead is to stabilize the lead using a ligature sleeve or suture sleeve secured to the lead body and attached to the superficial fascia with a suture as described, for example, in U.S. Pat. No. 5,957,968 to Belden and U.S. Pat. No. 7,930,039 to Olson. This technique, while commonly used, suffers from drawbacks including significant incidence of lead dislodgement. Another drawback is that the superficial tissue is often at an undesirable distance from the tissue targeted for stimulation. Any change in patient posture which results in a change in the relative distance between the superficial fascia and the stimulation target tissue may result in tension being applied to the lead body and subsequent movement of the electrodes.

U.S. Pat. Nos. 8,428,728 and 8,606,358 to Sachs and U.S. Patent Application Publication No. 2011/0224665 to Crosby et al., all assigned to the assignee of the present invention, and each of which is incorporated herein in their entireties by reference, describe implanted electrical stimulation devices that are designed to restore neural drive and rehabilitate the multifidus muscle to improve stability of the spine. Rather than masking pain signals while the patient's spinal stability potentially undergoes further deterioration, the stimulator systems described in those applications are designed to reactivate the motor control system and/or strengthen the muscles that stabilize the spinal column, which in turn is expected to reduce persistent or recurrent pain. Sachs and Crosby also describe in alternative embodiments peripheral nerve stimulation, in which electrical energy is applied to a nerve to effect a physiological change, such as to elicit a muscle contraction.

While the stimulator systems described in the Sachs patents and Crosby application seek to rehabilitate the multifidus and restore neural drive, use of those systems necessitates the implantation of one or more electrode leads in the vicinity of a predetermined anatomical site, such as the medial branch of the dorsal ramus of the spinal nerve to elicit contraction of the lumbar multifidus muscle. For that application, there is no convenient anatomical structure near the distal end of the lead to allow use of conventional anchoring mechanisms. Anchoring the lead to the superficial fascia as described above initially may be effective in many cases, but leads anchored in this manner may be susceptible to the problems of dislodgement and fatigue-induced fracture.

Previously-known efforts to overcome the problems of lead displacement abound. For example, U.S. Pat. No. 7,493,175 to Cates describes apparatus for subcutaneously anchoring a cardiac electrode lead using multiple tines. Such an apparatus would be undesirable for implantation in or adjacent to spinal muscle as the tines may become dislodged and tear the muscle during movement.

U.S. Pat. No. 7,797,053 to Atkinson describes a tether and a stent like device at the distal portion of a lead that may be expanded inside a cardiac vein to anchor a cardiac pacing lead. A similar stent-like anchor for a neurostimulation lead is described in U.S. Pat. No. 7,917,230 to Bly. U.S. Pat. No. 7,908,015 to Lazeroms describes a stimulation lead to be placed subcutaneously in which the fixation mechanism includes a movable mechanism at the distal end of the lead such that the lead diameter is increased at the distal end when engaged to provide anchoring. U.S. Pat. No. 8,170,690 to Morgan describes use of a helical element (screw) for anchoring a lead. These previously known anchoring systems are ill suited for neuromuscular stimulation because such systems have a high risk of dislodgement of the lead when implanted in or adjacent to muscle.

It therefore would be desirable to provide electrode leads and methods of implantation wherein the lead is securely anchored within a patient and is able to absorb axial movement and tensile load without distributing the load to the distal anchored end, thus reducing the risk of dislodgement of the lead and/or lead fracture.

IV. SUMMARY OF THE INVENTION

The present invention overcomes the drawbacks of previously-known systems by providing apparatus for neuromuscular electrical stimulation including an elongated member having a proximal region and a distal region, at least one conductor, and an insulative sheath surrounding at least a portion of the conductor. The elongated member further includes one or more electrodes disposed at the distal region of the elongated member, at least one fixation element disposed at the distal end of the elongated member, so as to secure the one or more electrodes in or adjacent to a desired anatomical site within a patient, and a strain relief portion on the proximal side of the one or more electrodes, so as to reduce transmission of axial loads to the distal region of the elongated member, thereby reducing the risk of fatigue fracture and displacement of the one or more electrodes.

The strain relief portion may be a portion that is elastic and may include a helical coil conductor. The elastic strain relief portion also may include a sheath of insulative material having a lower durometer than the surrounding insulative sheath, thereby allowing the elastic portion to stretch more than the surrounding portions of the elongated member.

The conductor of the elongated member may be a coiled conductor or a cable conductor.

The strain relief portion may include the insulative sheath of the elongated member having a bellowed configuration and the at least one conductor comprising a coiled conductor. The strain relief portion alternatively or additionally may include the elongated member having a sigmoid configuration. The strain relief portion alternatively or additionally may include the elongated member having a helical coiled configuration.

The strain relief portion may include a portion of the elongated member formed in a strain relief loop. The strain relief portion may be contained within a sealed pouch comprising a material which allows fluid ingression but reduces, or preferably prevents, tissue ingrowth.

The elongated member further may comprise a distal tip and a distal connection nut, wherein the first fixation element is moveable between a first insertion position and a second deployed position, and wherein the second deployed position is achieved when at least a portion of the distal tip is coupled to at least a portion of the distal connection nut. A distal tip locking stylet may be included to strengthen the connection between the distal tip and the distal connection nut against axial forces and the distal tip may have an internal aperture for receiving the locking stylet. The locking stylet may be coupled to the distal tip via a plurality of threads that engage with a counterpart plurality of threads on the internal aperture of the distal tip. The locking stylet also may be coupled to the distal tip via at least one engagement member biased radially inward to engage the locking stylet as it is inserted into the internal aperture.

In accordance with another aspect of the present invention, an apparatus for neuromuscular stimulation is provided including an elongated member having a proximal region and a distal region, at least one conductor, and an insulative sheath surrounding at least a portion of the conductor. The elongated member further includes one or more electrodes disposed at the distal region of the elongated member, at least one fixation element disposed at the distal end of the elongated member, so as to secure the one or more electrodes in or adjacent to a desired anatomical site within a patient, and a distal tip and a distal connection nut, wherein a first fixation element of the at least one fixation element is moveable between a first insertion position and a second deployed position, wherein the second deployed position is achieved when at least a portion of the distal tip is coupled to at least a portion of the distal connection nut. The apparatus also may include a distal tip locking stylet to strengthen the connection between the distal tip and the distal connection nut against axial forces, and the distal tip may have an internal aperture for receiving the locking stylet. The locking stylet may be coupled to the distal tip via a plurality of threads that engage with a counterpart plurality of threads on the internal aperture of the distal tip.

V. BRIEF DESCRIPTION OF THE DRAWINGS

FIG. 1 shows an exemplary electrode lead having at least one distal fixation element and a strain relief portion.

FIG. 2 depicts the distal region of an exemplary electrode lead having a strain relief portion comprising a helical conductor portion on a proximal side of the electrodes.

FIG. 3 depicts the distal region of an exemplary electrode lead having a portion comprising lead material of a lower durometer than the surrounding lead body.

FIG. 4 shows the distal region of an exemplary electrode lead having a bellowed portion.

FIG. 5 shows the distal region of an exemplary electrode lead having a sigmoid portion.

VI. DETAILED DESCRIPTION OF THE INVENTION

Figure 6:
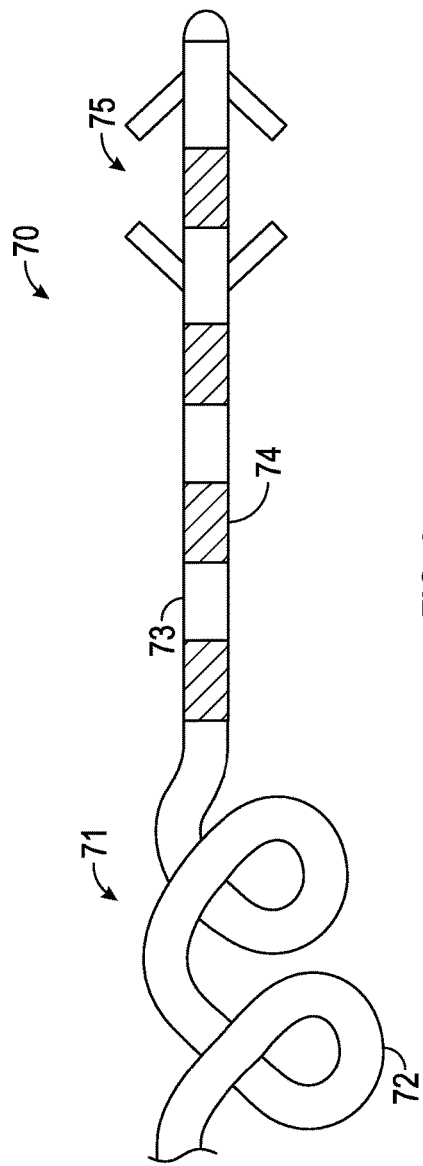
FIG. 6 shows the distal region of an exemplary electrode lead having a helical portion.

The neuromuscular stimulation lead of the present invention comprises a lead body having a strain relief portion and a plurality of electrodes configured to provide electrical stimulation from an implantable pulse generator to neuromuscular tissue located within a patient's back. The leads disclosed herein are particularly adapted for use in stimulating tissue associated with the lumbar spine for use in restoring muscle function and lumbar spine stability, while overcoming lead displacement and fatigue fracture issues observed with previously-known electrode lead designs.

Stimulation Lead with Strain Relief Portion

Referring to FIG. 1, exemplary stimulation lead 10 constructed in accordance with the principals of the present invention is described. Stimulation lead 10 includes proximal end 12, plurality of interior conductors 13, distal region 14, insulative sheath 15, electrodes 16, anchoring mechanism 18 including fixation elements 19a and 19b, and strain relief portion 20. Proximal end 12 of stimulation lead 10 is configured to be detachably attached to implantable pulse generator (IPG) 8 so that conductors 13 electrically couple IPG 8 to electrodes 16. Stimulation lead 10 illustratively has four electrodes 16, each coupled to a separate conductor 13

(only one shown), and are configured to be implanted in or adjacent to tissue, such as nervous tissue, muscle, ligament, and/or joint capsule.

Stimulation lead 10 is a suitable length for positioning electrodes 16 in or adjacent to target tissue while IPG 8 is implanted in a suitable location, e.g., the lower back. For example, stimulation lead 10 may be between about 30 and 80 cm in length, and preferably about 45 or about 65 cm in length. Stimulation lead 10 also has a diameter for placement within the muscles of the lumbar spine, for example, between about 1 and 2 mm in diameter and preferably about 1.3 mm.

Electrodes 16 may be configured to stimulate the tissue at a stimulation frequency and at a level and duration sufficient to cause muscle to contract and may be ring electrodes, partial electrodes, segmented electrodes, nerve cuff electrodes placed around the nerve innervating the target muscle, or the like. Electrodes 16 are a suitable length(s) and spaced apart a suitable distance along stimulation lead 10. For example, electrodes 16 may be about 2-5 mm in length, and preferably about 3 mm, and may be spaced apart about 2-6 mm, and preferably about 4 mm. As will also be understood by one of skill in the art, a stimulation lead may contain more or fewer than the four electrodes shown.

In the embodiment of FIG. 1, anchoring mechanism 18 includes fixation elements 19a and 19b, illustratively tines, which are configured to bracket an anchor site, e.g., muscle, therebetween to secure stimulation lead 10 at a target site without damaging the anchor site. Proximal fixation elements 19a are angled distally to resist motion in the distal direction and reduce the risk of over-insertion or migration of the lead in the distal direction. Distal fixation elements 19b are angled proximally and are configured to be deployed on the distal side of the tissue immediately adjacent to the target of stimulation. Fixation elements 19a and 19b accordingly reduce the risk of migration both proximally and distally.

The length of and spacing between the fixation elements is defined by the structure around which the fixation elements are to be placed. In one embodiment, the length of each fixation element is between about 1.5-4 mm and preferably about 2.5 mm and the spacing is between about 2 mm and 10 mm and preferably about 6 mm. Proximal and distal fixation elements 19a and 19b are configured to collapse inward toward stimulation lead 10 in a delivery state and to expand in a deployed state. Other fixation elements suitable for use in anchoring stimulation lead 10 of the present invention are described in U.S. Patent Application Pub. No. 2013/0131766 to Crosby and U.S. Patent Application Pub. No. 2013/0338730 to Shiroff, both assigned to the assignee of the present invention, the entire contents of each of which is incorporated herein by reference.

It was observed that during initial clinical testing involving the neuromuscular stimulation of the multifidus muscles of the lumbar spine with IPG 8 and conventional electrode leads, the leads frequently would dislodge and/or fracture after relatively short implantation periods. This was believed to be caused by the lack of suitable anchor sites for the stimulation leads, and also due to the torsional and bending stresses imposed on the stimulation leads by movement of the surrounding muscles. To address these issues, stimulation lead 10 therefore includes strain relief portion 20, which is configured to reduce axial strain on anchoring mechanism 18. In particular, as described below, strain relief portion 20 may take on a variety of structures that are designed to reduce the strain on stimulation lead 10 and anchoring mechanism 18, thereby reducing the risk of lead dislodgement, fatigue fracture, and injury to the tissue through which stimulation lead 10 passes. Each of the embodiments discussed below incorporates a strain relief portion 20, 31, 41, 51, 61, 71, 81 configured to be stretched or extended in response to axial displacements of the proximal part of the lead, and also to accommodate local flexion of, for example, the lumbar spine muscles that may cause localized lateral displacements of the stimulation lead.

Referring now to FIG. 2, stimulation lead 30 is described in which strain relief portion 31 comprises helical conductor 32. Helical conductor 32 preferably comprises a plurality of insulated wires that couple to the individual electrodes 33 and are enclosed within insulative sheath 34. Stimulation lead 30 further comprises lead body portions 35a and 35b, and anchoring mechanism 36, similar in design to anchoring mechanism 18 of FIG. 1. Anchoring mechanism 36 includes distally-directed tines 37a and proximally-directed tines 37b that are deployed, e.g., by proximally retracting a delivery sheath (not shown) during placement of the distal region of stimulation electrode 30.

Referring to FIG. 3, stimulation lead 40 is constructed similarly to stimulation lead 30 of FIG. 2, except that strain relief portion 41 comprises helical conductor 42 (shown in dotted line) enclosed in a stretchable length of insulating tubing 43, so as to reduce, or preferably prevent tissue ingrowth that could reduce the elastic functionality of helical conductor 41. In particular, insulating tubing 43 may comprise a portion of tubing having lower durometer than the surrounding portions of tubing 44a and 44b. Accordingly, the combination of helical conductor 42 and portion of lower durometer tubing 43 may provide the elastic functionality of the strain relief portion. Other components of stimulation lead 40 include plurality of electrodes 45, and anchoring mechanism 46 comprising tines 47a and 47b, as discussed for the preceding embodiment.

FIG. 4 depicts an alternative embodiment of stimulation lead 50 having strain relief portion 51 comprising insulated tubing 52 having a bellows configuration. As for the embodiments of FIGS. 2 and 3, plurality of helical conductors 53 (one shown in dotted line) are provided to electrically couple electrodes 54 on body portion 55b to the proximal body portion 55a. As discussed above for the previous embodiments, stimulation lead 50 includes anchoring mechanism 56, preferably comprising deployable angled tines 57a and 57b.

Referring now to FIGS. 5 and 6, further alternative embodiments of stimulation leads including strain relief portions constructed in accordance with the present invention are described. In particular, FIG. 5 shows stimulation lead 60 having strain relief portion 61 comprising insulated tubing 62 formed in a sigmoid configuration that can be elastically stretched to a straightened form in response to the application of axial, lateral or torsional loads to stimulation lead 60. Other components of stimulation lead 60, including distal body portion 63, electrodes 64, and anchoring mechanism 65 may be constructed as described above for the preceding embodiments.

Figure 7:
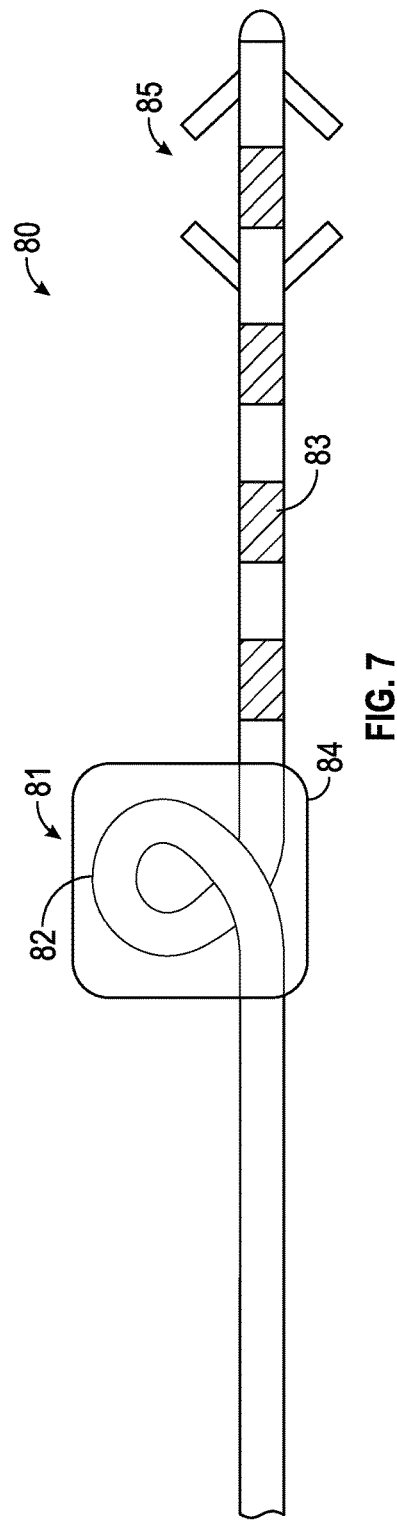
FIG. 7 shows the distal region of an exemplary electrode having a strain relief loop formed therein and contained within a pouch.

Similarly, FIG. 6 depicts stimulation lead 70 having strain relief portion 71 comprising insulated tubing 72 formed in a coiled configuration that can be stretched in response to strains on the stimulation lead 70. Other components of stimulation lead 70, including distal body portion 73, electrodes 74, and anchoring mechanism 75 may be constructed as described above. Each of the embodiments in FIGS. 5 and 6 may include electrical conductors that match the shape of the sigmoid or coiled strain relief portion of the respective stimulation leads. In FIG. 7, strain relief portion 81 of stimulation lead 80 comprises loop 82 of tubing containing electrical conductors that couple electrodes 83 to the proximal end of stimulation lead 80. Loop 82 is enclosed within sealed biocompatible elastomeric capsule 84. As with the preceding embodiments, loop 82 and capsule 84 permit extension of the stimulation lead between its proximal and distal ends without imposing excessive loads on anchoring mechanism 85 that could result in axial displacement of electrodes 83. In alternative embodiments, the capsule 84 may enclose a portion of the lead 80 having a sigmoid or helical coil configuration, as described above, or another configuration capable of extending in the axial direction. Elastomeric capsule preferably is watertight, but in some embodiments may permit fluid ingress so long as the capsule material reduces the opportunity for or prevents tissue ingrowth or tissue adhesion to the capsule that could limit the strain relief functionality of loop 82.

Deployable Fixation Elements

Additional limitations to the effect of tensile loading on the distal end of a stimulation lead may be provided through additional support mechanisms for maintaining the fixation elements.

Figure 8A:
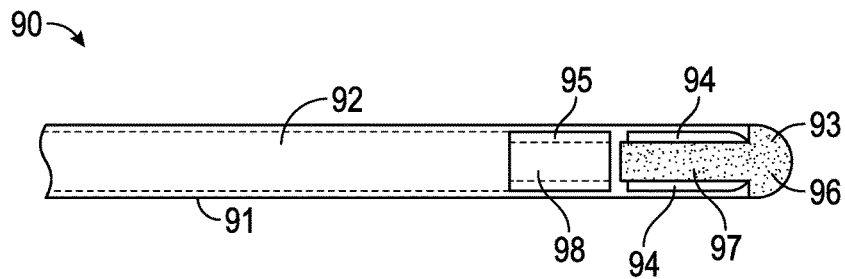
FIGS. 8A and 8B depict, respectively, the distal region of an exemplary electrode having deployable fixation elements in a first insertion position where a distal tip is separated from a distal connection nut and in a second deployed position where a distal tip is coupled with a distal connection nut.
Figure 8B:
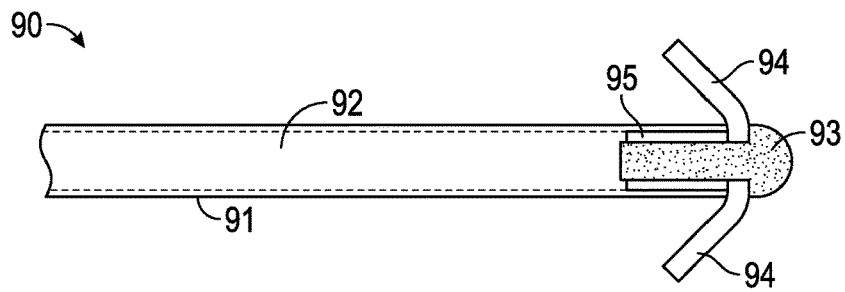

As shown in FIGS. 8A and 8B, a stimulation lead according to the present invention is provided. Stimulation lead 90 may include elongated body 91 having stylet lumen 92 extending therethrough, distal tip 93, expandable fixation elements 94, and nut 95. Stylet lumen 92 is shaped and sized to permit a stylet to be inserted therein, for example, during delivery of stimulation lead 90. Distal tip 93 has blunt head 96 configured to permit blunt dissection of tissue as lead 90 is inserted therethrough, and narrow body 97 sized for insertion in stylet lumen 92 such that blunt head 96 sealingly contacts the distal end of body 91. In one embodiment, distal tip 93 may be used to prevent the stylet from extending distally out of stylet lumen 92 beyond the distal end of the stimulation lead 90. Expandable fixation element 94 are configured to transition from a delivery state, shown in FIG. 8A, to a deployed state, shown in FIG. 8B. In the deployed state, expandable fixation elements 94 contact tissue and anchor lead 90 at a target location. Expandable fixation elements 94 are coupled to distal tip 93 and are sized to fit within stylet lumen 92 between narrow body 97 and body 91 in the deployed state while having a length suitable for anchoring in tissue in the deployed state. Nut 95 may be sized to fit within stylet lumen 92 and may be coupled to body 91 within lumen 92. Nut 95 includes lumen 98 sized to receive narrow body 97.

The present invention provides embodiments for deploying fixation elements actively as shown in FIGS. 8A and 8B. FIG. 8A depicts the distal region of an exemplary stimulation lead having an expandable fixation element shown in a delivery state. Distal tip 93 is disposed at the distal end of elongated member 91. The proximal end of distal tip 93 interfaces with nut 95, also joined to stimulation lead 90, but more proximally. Between distal tip 93 and nut 95, stimulation lead 90 has longitudinal slits at each expandable fixation element 94 allowing elements 94 to move through the slits during deployment. Upon deployment of the electrode lead, depicted in FIG. 8B, distal tip 93 is driven proximally through nut lumen 98 within stimulation lead 90. As distal tip 93 moves proximally, the distal end of nut 95 contacts elements 94 and urges elements 94 to expand outwardly, as shown in FIG. 8B. Elements 94 may be located to provide stabilization within a tissue plane or between two adjacent tissue planes.

Figure 9:
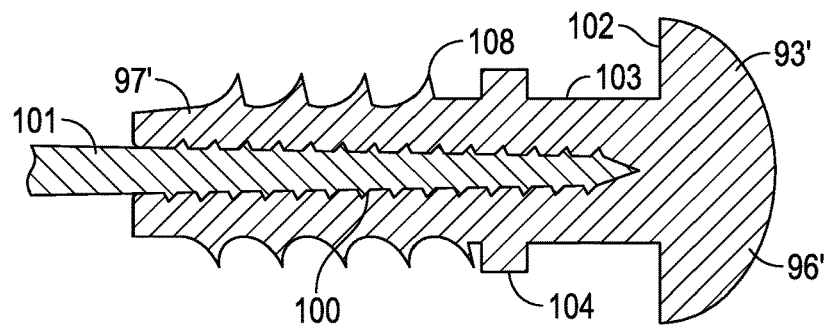
FIG. 9 is side sectional view of an exemplary distal tip having a threaded locking stylet inserted therein.

FIG. 9 illustrates an alternative distal tip 93' for use in stimulation lead 90 of FIGS. 8A and 8B, wherein like components are identified by like-primed reference numbers. Distal tip 93', includes ledge 102 of head 96', groove 103, ring 104, and coupling mechanism 105. Such features of distal tip 93' may also be present in the distal tip 93 of FIGS. 8A and 8B. Ledge 102 is configured to contact the distal end of the lead body. Groove 103 is configured to accept elements 94 for coupling. Ring 104 protrudes from narrow body 97' such that elements 94 are disposed in groove 103 between ring 104 and ledge 102. Narrow body 97' includes coupling mechanism 105, such as threads, ribs, or the like, for coupling distal tip 93' to nut 95. Alternative distal tip 93' further includes a threaded internal opening 100 configured to permit coupling to stylet 101 to provide axial strength for tensile loading during delivery and extraction by distributing forces over a large area of the fixation elements (and/or features of the lead and/or the lead itself) and to permit distal tip 93' to be moved proximally by pulling stylet 101 proximally. Such distribution of force is expected to reduce the risk of lead fracture during delivery and extraction.

Figure 10:
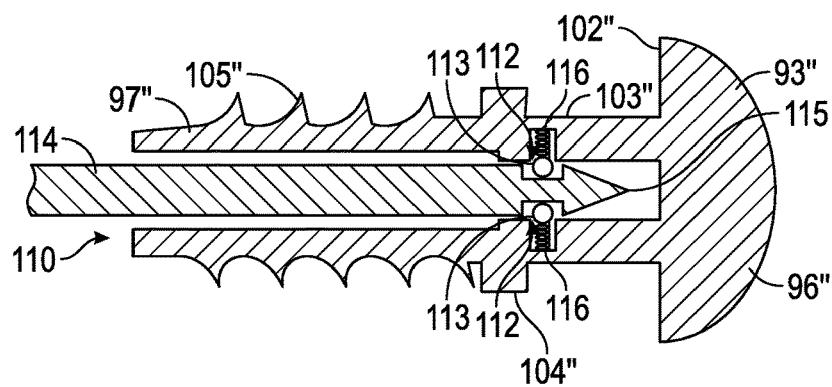
FIG. 10 is a side sectional view of an exemplary distal tip having a spring loaded locking element and a tapered locking stylet inserted therein.

Referring now to FIG. 10, another alternative distal tip 93" for use in stimulation lead 90 is provided. As will be observed by comparing FIGS. 9 and 10, distal tip 93" is similar to distal tip 93' and includes opening 110 rather than threaded opening 100, and locking groove 111, springs 112, and bearing 113. Opening 110 is configured to receive locking stylet 114 having tapered tip 115 and groove 116 proximal to tapered tip 115. Distal tip 93" has a spring loaded mechanism for locking onto tapered stylet 114, illustratively ball bearings 113 coupled to respective springs 112 which are disposed in grooves 111 in opening 110 of narrow body 97". Ball bearings 113 are biased inwardly by respective springs 112 which can be moved into groove 116 formed in tapered stylet 114 when stylet is inserted into opening 110, thereby locking stylet 114 in place. Groove 116 may be a single, bounded aperture in a portion of stylet 114, or may be a ridge formed about the full circumference of stylet 114. Stylet 114 is configured to provide axial strength for tensile loading during delivery and extraction by distributing forces over a large area of the fixation elements (and/or features of the lead and/or the lead itself) and to permit distal tip 93" to be moved proximally by pulling stylet 114 proximally to, for example, expand the expandable fixation elements.

Other locking stylets used for locking the distal tip into the position shown in FIGS. 8B and 10 may be used according to the present invention for supporting the expansion of the fixation elements and thereby supporting the position of the distal end of the stimulation lead at a desired stimulation site. In addition, as will be readily apparent to one of ordinary skill in the art, distal tips 93' and 93" may be used in embodiments of FIGS. 1-7 with stylets without departing from the scope of the present invention.

Figure 11:
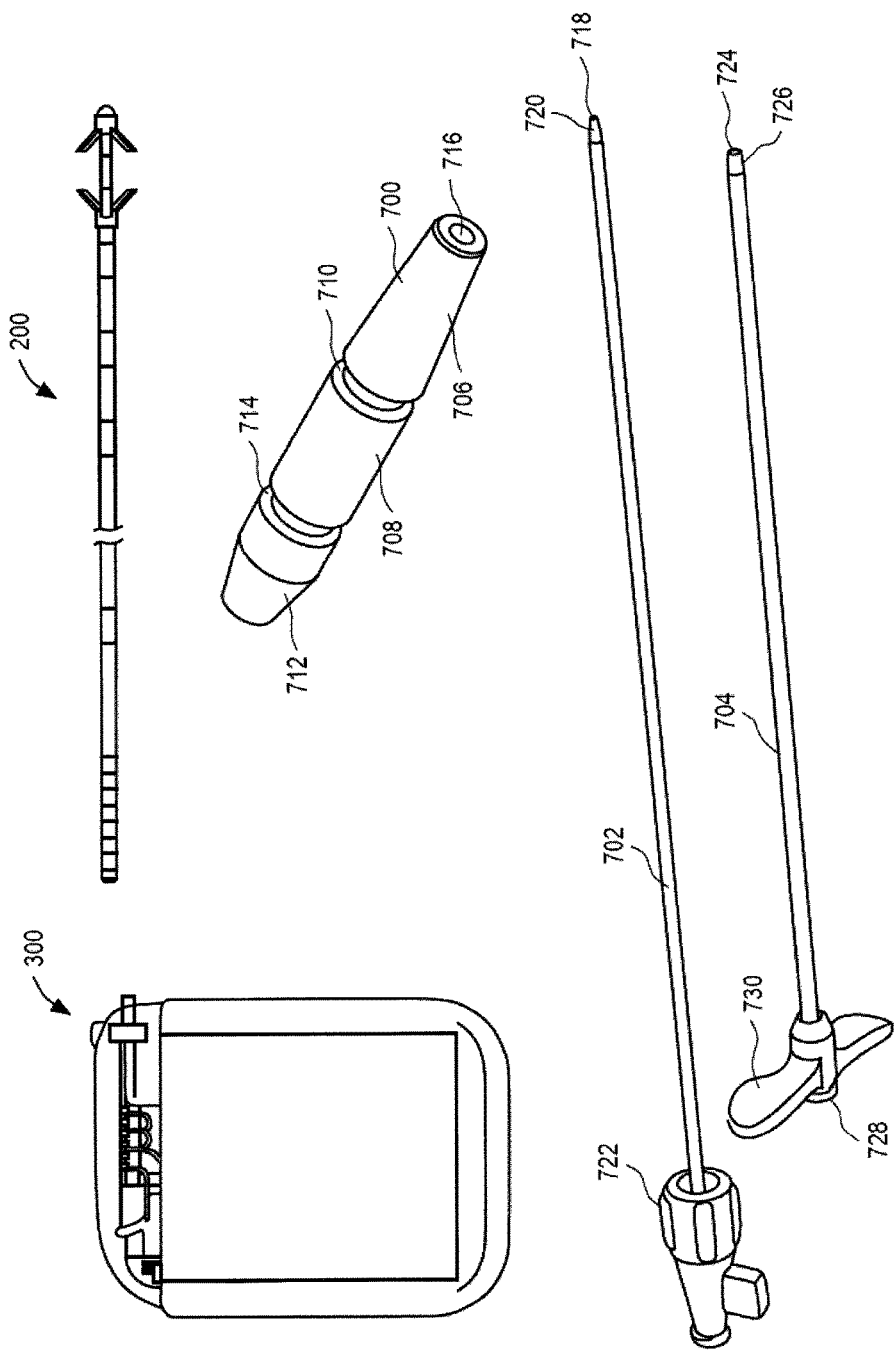
FIG. 11 illustrates an exemplary system for implanting an electrode lead and IPG in accordance with the principles of the present invention.

Referring now to FIG. 11, an exemplary method for implanting an electrode lead and IPG is described. First, electrode lead 200, IPG 300, stylet (not shown), suture sleeve 700, introducer 702, and dilator 704 are provided, as shown in FIG. 11. In FIG. 11, components of the system are not depicted to scale on either a relative or absolute basis. Suture sleeve 700 illustratively includes first end section 706, middle section 708 separated from first end section by first groove 710, second end section 712 separated from middle section 708 by second groove 714, and sleeve lumen 716. First and second end sections 706 and 712 may have truncated conical portions as shown. First and second grooves 710 and 714 are sized and shaped to accept sutures such that suture sleeve 700 may be secured to tissue, e.g., superficial fascia, using the sutures. Sleeve lumen 716 is sized such that electrode lead 200 may be inserted therethrough.

Introducer 702 may include introducer lumen 718, distal tip 720, and coupling portion 722. Introducer lumen 718 extends through introducer 702 and is shaped and sized to permit electrode lead 200 to slide therethrough. Distal tip 720 is beveled to ease introduction through tissue. Coupling portion 722, illustratively a female end with threads, is configured to be coupled to a portion of dilator 704. In one embodiment, introducer 702 comprises a commercially available 7 French (Fr) introducer.

Dilator 704 may include dilator lumen 724, distal tip 726, coupling portion 728, and handle 730. Dilator lumen 724 extends through dilator 704 and is shaped and sized to permit introducer 702 to slide therethrough. Distal tip 726 is beveled to ease introduction through tissue. Coupling portion 728, illustratively a male end with threads, is configured to be coupled to a portion of introducer 702, e.g., coupling portion 722. Handle 730 is sized and shaped to permit a physician to comfortably hold dilator 704.

Next, a stylet is inserted within the stylet lumen of electrode lead 200 to provide additional stiffness to electrode lead 200 to ease passage of electrode lead 200 through introducer 702. The stylet may be a commercially available stylet such as a locking stylet available from Cook Group Incorporated of Bloomington, Ind. Electrode lead 200 then is inserted within introducer lumen 718 of introducer 702.

Using fluoroscopy, acoustic, anatomic, or CT guidance, dilator 704 is delivered transcutaneously and transmuscularly to a target site, e.g., in or adjacent to tissue associated with control of the lumbar spine. Such tissue may include nervous tissue, muscle, ligament, and/or joint capsule. In one embodiment, muscle includes skeletal muscle such as the multifidus, transverse abdominus, quadratus lumborum, psoas major, internus abdominus, obliquus externus abdominus, and erector spinae muscles and nervous tissue includes a peripheral nerve that innervates skeletal muscle. In a preferred embodiment, nervous tissue comprises the dorsal ramus nerve, or fascicles thereof, that innervate the multifidus muscle.

Next, introducer 702 (having a portion of the electrode lead disposed therein) is inserted through dilator lumen 724 to the target site. Introducer 702 may then be coupled to dilator 704, e.g., by screwing coupling portion 722 onto coupling portion 728.

A segment of a typical human lumbar spine shown has a vertebral body V, transverse process TP, inter-transverse ligament ITL, and a dorsal ramus DR. Dilator 704 having introducer 702 disposed therethrough, which has a portion of the electrode lead disposed therein, are positioned adjacent to the target site, the medial branch of the dorsal ramus DR nerve that innervates the multifidus muscle. In one embodiment, electrodes of the electrode lead are positioned to stimulate the medial branch of the dorsal ramus that exits between the L2 and L3 lumbar segments and passes over the transverse process of the L3 vertebra, thereby eliciting contraction of fascicles of the lumbar multifidus at the L3, L4, L5 and Si segments and in some patients also at the L2 segment.

Introducer 702 and dilator 704 are moved proximally, e.g., using handle 730, while maintaining the position of electrode lead 200 at the target site. The first and second fixation elements of electrode lead 200 individually transition from a collapsed state within introducer 702 to an expanded state, as introducer 702 passes over the respective fixation element. The first and second fixation elements sandwich an anchor site, e.g., muscle, therebetween without damaging the anchor site in the expanded state to fix electrode lead 200 at the target site.

Introducer 702 and dilator 704 are moved proximally off the proximal end of electrode lead 200 and suture sleeve 700 is placed over the proximal end of electrode lead 200 and moved distally. When suture sleeve 700 is positioned adjacent to the superficial fascia SF beneath skin SK, sutures are sewn into the first and second grooves of suture sleeve 700 so as to secure suture sleeve 700 to the superficial fascia SF.

Finally, the IPG is coupled to the proximal end of electrode lead 200 and implanted within the lower back of the patient.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. A method of implanting a lead for neuromuscular electrical simulation, the method comprising:
   implanting a distal region of the lead in or adjacent to tissue associated with control of the lumbar spine within a patient, the lead consisting of:
      an elongated member having a proximal end, a distal region, a plurality of electrodes and an anchoring mechanism disposed on the distal region, and a plurality of electrical conductors extending between the plurality of electrodes and the proximal end;
      a strain relief portion consisting of an insulated loop of the elongated member disposed proximal of and spaced apart from the plurality of electrodes, the strain relief portion configured to reduce transmission of axial and lateral loads applied to the distal region of the elongated member and the anchoring mechanism; and
      a suture sleeve consisting of a first end section having a truncated conical shape, a second end section having a truncated conical shape, a middle section between the first and second end sections, a first groove between the first end section and the middle section, a second groove between the middle section and the second end section, and a sleeve lumen extending through the suture sleeve, the sleeve lumen sized to permit passage of the proximal end of the elongated member therethrough, each of the first and second grooves configured to accept a suture to secure the suture sleeve to tissue beneath the skin,
   wherein the anchoring mechanism includes distal fixation elements angled proximally relative to the elongated member and proximal fixation elements angled distally relative to the elongated member such that the distal and proximal fixation elements are angled towards one another to secure the plurality of electrodes in or adjacent to tissue associated with control of the lumbar spine within a patient.

2. The method of claim 1, wherein a portion of the strain relief portion is elastic.

3. The method of claim 1, wherein the plurality of electrical conductors are a plurality of helical coil conductors.

4. The method of claim 1, wherein the distal and proximal fixation elements are deployable tines.

5. The method of claim 1, wherein a portion of the plurality of electrical conductors is coiled.

6. The method of claim 1, wherein implanting the distal region of the lead comprises implanting the plurality of electrodes in or adjacent to at least one of nervous tissue, a muscle, a ligament, or a joint capsule.

7. The method of claim 1, further comprising stimulating with at least one of the plurality of electrodes a dorsal ramus nerve that innervates a multifidus muscle.

8. The method of claim 1, wherein a portion of the plurality of electrical conductors is extendable.

9. The method of claim 1, wherein implanting the distal region of the lead further comprises moving the anchoring mechanism between a first insertion position and a second deployed position.

10. The method of claim 1, wherein implanting the distal region of the lead comprises deploying the anchoring mechanism between muscle layers.

11. The method of claim 1, further comprising securing the elongated member to a superficial fascia within the patient using the suture sleeve.

12. The method of claim 1, wherein implanting the distal region of the lead comprises implanting at least one of the plurality of electrodes in or adjacent to nervous tissue.

13. A method of implanting a lead for neuromuscular electrical simulation, the method comprising:
 implanting a distal region of the lead in or adjacent to tissue associated with control of the lumbar spine within a patient, the lead consisting of:
  an elongated member having a proximal end, a distal region, a plurality of electrodes and an anchoring mechanism disposed on the distal region, and a plurality of electrical conductors extending between the plurality of electrodes and the proximal end; and
  a strain relief portion consisting of an insulated loop of the elongated member disposed proximal of and spaced apart from the plurality of electrodes, the strain relief portion configured to reduce transmission of axial and lateral loads applied to the distal region of the elongated member and the anchoring mechanism,
 wherein the anchoring mechanism includes distal fixation elements angled proximally relative to the elongated member and proximal fixation elements angled distally relative to the elongated member such that the distal and proximal fixation elements are angled towards one another to secure the plurality of electrodes in or adjacent to tissue associated with control of the lumbar spine within a patient.

14. The method of claim 13, wherein a portion of the strain relief portion is elastic.

15. The method of claim 13, wherein the plurality of electrical conductors are a plurality of helical coil conductors.

16. The method of claim 13, wherein the distal and proximal fixation elements are deployable tines.

17. The method of claim 13, wherein a portion of the plurality of electrical conductors is coiled.

18. The method of claim 13, wherein implanting the distal region of the lead comprises implanting the plurality of electrodes in or adjacent to at least one of nervous tissue, a muscle, a ligament, or a joint capsule.

19. The method of claim 13, further comprising stimulating with at least one of the plurality of electrodes a dorsal ramus nerve that innervates a multifidus muscle.

20. The method of claim 13, wherein a portion of the plurality of electrical conductors is extendable.

21. The method of claim 13, wherein implanting the distal region of the lead further comprises moving the anchoring mechanism between a first insertion position and a second deployed position.

22. The method of claim 13, wherein implanting the distal region of the lead comprises deploying the anchoring mechanism between muscle layers.

23. The method of claim 13, wherein implanting the distal region of the lead comprises implanting at least one of the plurality of electrodes in or adjacent to nervous tissue.

* * * * *